(12) United States Patent
Merkel et al.

(10) Patent No.: US 8,293,954 B2
(45) Date of Patent: Oct. 23, 2012

(54) CATALYST LIFE IMPROVEMENT FOR THE VAPOR PHASE MANUFACTURE OF 1-CHLORO-3,3,3-TRIFLUOROPROPENE

(75) Inventors: Daniel C. Merkel, Orchard Park, NY (US); Konstantin A. Pokrovski, Orchard Park, NY (US); Hsueh Sung Tung, Getzille, NY (US)

(73) Assignee: Honeywell International Inc., Morristown, NJ (US)

( * ) Notice: Subject to any disclaimer, the term of this patent is extended or adjusted under 35 U.S.C. 154(b) by 380 days.

(21) Appl. No.: 12/720,763

(22) Filed: Mar. 10, 2010

(65) Prior Publication Data

US 2011/0224465 A1    Sep. 15, 2011

(51) Int. Cl.
*C07C 17/00*    (2006.01)
(52) U.S. Cl. ........................................ 570/156; 570/161
(58) Field of Classification Search .................. 570/156, 570/161

See application file for complete search history.

(56) References Cited

U.S. PATENT DOCUMENTS

| | | | |
|---|---|---|---|
| 5,710,352 | A | 1/1998 | Tung |
| 5,811,603 | A | 9/1998 | Elsheikh |
| 6,111,150 | A | 8/2000 | Sakyu et al. |
| 6,235,951 | B1 | 5/2001 | Sakyu et al. |
| 6,316,681 | B1 | 11/2001 | Yoshikawa et al. |
| 6,844,475 | B1 | 1/2005 | Tung et al. |
| 2005/0020863 | A1 | 1/2005 | Tung et al. |
| 2009/0030244 | A1 | 1/2009 | Merkel et al. |
| 2009/0105510 | A1 | 4/2009 | Quan et al. |
| 2009/0270661 | A1 | 10/2009 | Wang et al. |

FOREIGN PATENT DOCUMENTS

GB    2313118 A    11/1997

*Primary Examiner* — Jafar Parsa
(74) *Attorney, Agent, or Firm* — Bruce O. Bradford

(57) ABSTRACT

This invention achieves a catalyst life improvement for the catalyzed vapor phase reaction of 1,1,1,3,3-pentachloropropane with hydrogen fluoride to form 1-chloro-3,3,3-trifluoropropene by introducing an oxygen co-feed into the fluorination reactor. By introduction of an oxygen co-feed to the reactor feed, the catalyst life was extended a minimum of two-fold (2×).

20 Claims, 2 Drawing Sheets

CATALYST LIFE IMPROVEMENT FOR THE VAPOR PHASE MANUFACTURE OF 1-CHLORO-3,3,3-TRIFLUOROPROPENE

BACKGROUND OF THE INVENTION

The compound E-1-chloro-3,3,3-trifluoropropene (HCFO-1233zd(E)) is a next generation liquid low global warming potential (LGWP) foam blowing agent, refrigerant and solvent. This compound has the following structure:

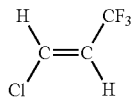

HCFO-1233zd(E) is a known compound. It can be produced in a vapor phase reaction as taught in U.S. Pat. No. 5,710,352; or it can be produced in a liquid phase reaction as taught in U.S. Pat. No. 6,844,475. These patents are hereby incorporated herein by reference in their entirety.

The deactivation of chromium oxide catalyst during fluorination of HCC-240fa is described in U.S. Pat. No. 5,710,352. According to U.S. Pat. No. 5,811,603, catalyst stability during the vapor phase fluorination of 1,1,3,3-tetrachloropropene (HCFO-1230za) with HF to produce 1,1,1,3,3-pentafluoropropane and 1-chloro-3,3,3-trifluoropropene can be improved by co-feeding oxygen or chlorine into the reactor.

The use of chlorofluorocarbons and hydrochlorofluorocarbons as foam blowing agents has been banned due to concerns that their release to atmosphere damages ozone layer. More recently, foam blowing has been accomplished through use of HFC-245fa; however, concern has been raised about global warming potential of this material. A leading candidate to replace HFC-245fa in foam blowing applications is E-1-chloro-3,3,3-trifluoropropene (HCFO-1233zd(E)). This material also has a potential use as a refrigerant, solvent or degreaser.

The compound E-1-chloro-3,3,3-trifluoropropene (HCFO-1233zd(E)) has no substantial ozone depletion potential (ODP), preferably an ODP of not greater than about 0.5 and even more preferably an ODP of not greater than about 0.25, most preferably an ODP of not greater than about 0.1; a global warming potential (GWP) of not greater than about 150, and even more preferably, a GWP of not greater than about 50.

As used herein, ODP is defined in the "Scientific Assessment of Ozone Depletion, 2002," a report of the World Meteorological association, incorporated here by reference.

As used herein, GWP is defined relative to that of carbon dioxide and over a 100 year time horizon, and defined in the same reference as for the ODP mentioned above.

The method of the present invention is part of a continued search for the next generation of low global warming potential materials. Such materials must have low environmental impact, as measured by global warming potential and ozone depletion potential.

SUMMARY OF THE INVENTION

E-1-chloro-3,3,3-trifluoropropene (HCFO-1233zd(E)) can be manufactured via fluorination of 1,1,1,3,3-pentachloropropane (HCC-240fa) with anhydrous hydrogen fluoride (HF). The reaction preferably takes place in the vapor phase using a fluorination catalyst consisting of partially fluorinated $Cr_2O_3$.

During initial reaction studies it was discovered that the catalyst life was very short in comparison to other fluorination reactions that incorporate the same catalyst. These initial studies indicated that a deactivated catalyst can be successfully regenerated using dilute oxygen. However, this method for regeneration of the catalyst requires the shut down of the reactor, resulting in a loss of production time. The present inventors have surprisingly found that upon introduction of an oxygen co-feed to the reactor feed, the catalyst life was extended a minimum of two times (2×).

In one embodiment of the invention, chromium oxide catalyst life during fluorination of HCC-240fa with HF to produce HCFO-1233zd(E) is significantly increased (i.e., a minimum two fold increase of catalyst life) when an oxygen co-feed is introduced into the fluorination reactor with the feeds of the raw materials, HCC-240fa and HF. This is advantageous because a slower catalyst deactivation by including an oxygen co-feed minimizes the loss in production time due to the need to regenerate the catalyst off-line. The source of oxygen can be oxygen gas, dry air, or oxygen gas diluted with inert gas such as nitrogen, argon, or helium.

Accordingly, one embodiment of the present invention is a method of extending the lifetime of a catalyst used in the vapor phase catalytic fluorination reaction of the raw materials 1,1,1,3,3-pentachloropropane (HCC-240fa) and hydrogen fluoride (HF) to produce 1-chloro-3,3,3-trifluoropropene, wherein the catalyst life is extended by at least two-fold, by introducing an oxygen co-feed into the fluorination reaction.

The reaction of HCC-240fa with HF to form HCFO-1233zd is an exothermic reaction. The present inventors have further discovered a correlation between the rate of catalyst deactivation during the reaction of HCC-240fa with HF and the rate of the temperature change inside the catalyst bed. In addition, an active catalyst exhibits a large exotherm relative to the external reactor heater. As the catalyst deactivates, the exotherm diminishes, and the temperature inside the deactivated catalyst bed approaches that of the external heater. Monitoring this change in the exotherm allows the reactor operator to add the oxygen co-feed to the reactor feed, to keep the catalyst from being deactivated for a longer period of time.

Accordingly, another embodiment of the present invention is a method of extending the lifetime of a catalyst used in the vapor phase catalytic fluorination reaction of the raw materials 1,1,1,3,3-pentachloropropane (HCC-240fa) and hydrogen fluoride (HF) to produce 1-chloro-3,3,3-trifluoropropene, wherein the catalyst life is extended by monitoring the exotherm of the active catalyst relative to the external reactor heater, and adding an oxygen co-feed into the fluorination reaction to keep the catalyst from being deactivated for up to two-times longer than when no oxygen co-feed is employed.

In certain embodiments of these methods, the source of oxygen may be selected from the group consisting of oxygen gas, dry air, oxygen gas diluted with an inert gas.

In certain embodiments of these methods, the catalyst may be selected from the group consisting of chromium, aluminum, cobalt, manganese, nickel and iron oxides, hydroxides, halides, oxyhalides, inorganic salts thereof and their mixtures.

In certain embodiments of these methods, the catalyst is selected from the group consisting of $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof.

In certain embodiments of these methods, the catalyst is selected from the group consisting of $FeCl_3$, $SnCl_4$, $TaCl_5$, $SbCl_3$, $AlCl_3$, and $AlF_3$, supported on carbon.

In certain embodiments of these methods, the catalyst is selected from the group consisting of $FeCl_3$, $SnCl_4$, $TaCl_5$, $SbCl_3$, $AlCl_3$, and $AlF_3$, supported on alumina.

In certain embodiments of these methods, the catalyst is selected from the group consisting of $FeCl_3$, $SnCl_4$, $TaCl_5$, $SbCl_3$, $AlCl_3$, and $AlF_3$, supported on fluorinated alumina.

In one preferred embodiment of both methods, the oxygen is introduced together with the feeds of the raw materials HCC-240fa and HF.

In another preferred embodiment of both methods, the oxygen is introduced after the raw materials HCC-240fa and HF have been vaporized.

In one preferred method, the catalyst comprises one or more chromium (III) oxides. More preferably, the catalyst comprises crystalline chromium oxide. Most preferably, the catalyst comprises amorphous chromium oxide. In especially preferred embodiments, the catalyst is at least partially fluorinated.

DETAILED DESCRIPTION OF THE INVENTION

Figure 1:
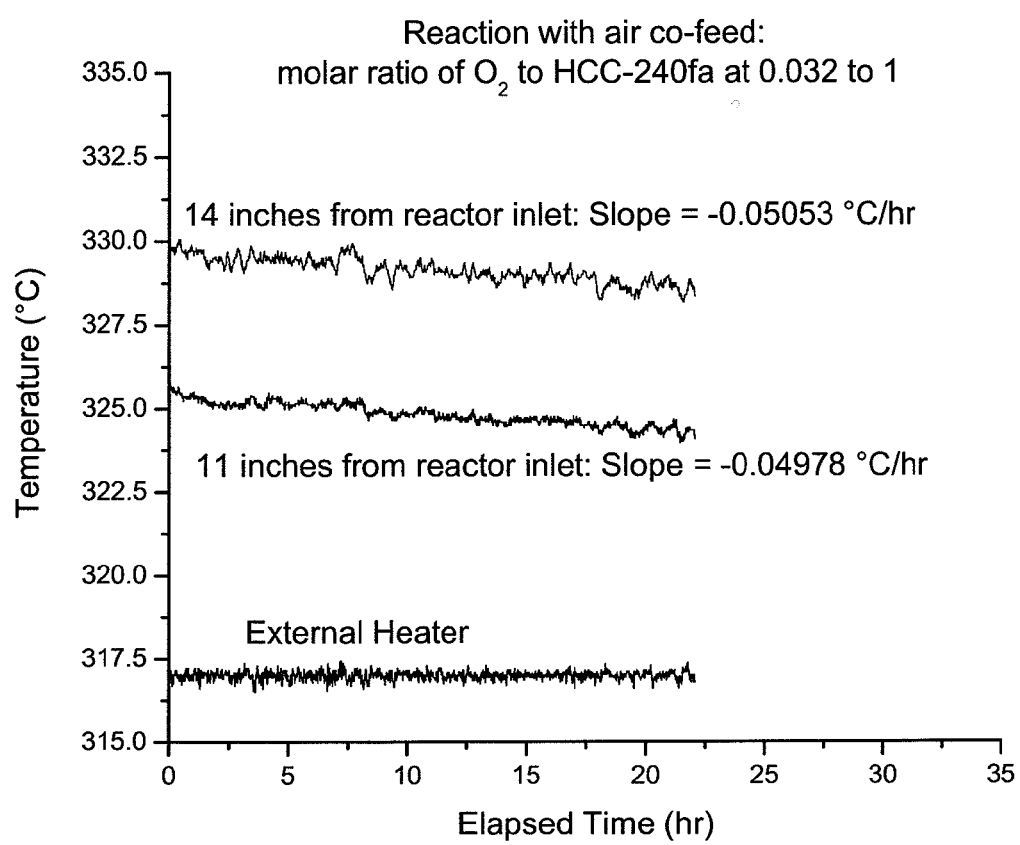
FIG. 1 illustrates the temperature profiles in the reactor with an air co-feed as measured at 11 and 14 inches from the inlet, compared to the temperature of the external sand bath heater over time.

As described above, E-1-chloro-3,3,3-trifluoropropene (HCFO-1233zd(E)) can be manufactured via fluorination of 1,1,1,3,3-pentachloropropane (HCC-240fa) with anhydrous hydrogen fluoride (HF). The reaction takes place in the vapor phase reactor using a fluorination catalyst consisting of partially fluorinated $Cr_2O_3$.

The Basic Reaction:

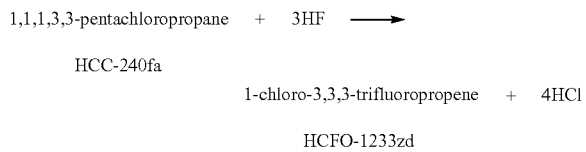

1,1,1,3,3-pentachloropropane + 3HF ⟶

HCC-240fa 1-chloro-3,3,3-trifluoropropene + 4HCl

HCFO-1233zd

During the fluorination of HCC-240fa with HF to produce HCFO-1233zd(E), a vapor phase reactor is first loaded with a fluorination catalyst from the group consisting of, but not limited to, chromium, aluminum, cobalt, manganese, nickel and iron oxides, hydroxides, halides, oxyhalides, inorganic salts thereof and their mixtures. All of the listed catalysts may be partially or totally fluorinated by anhydrous HF.

Catalysts can either be supported or in bulk. Combinations of catalysts suitable for the present invention nonexclusively include $Cr_2O_3$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. All of the listed catalysts may be partially or totally fluorinated by anhydrous HF.

Additional fluorination catalysts that can be used include $FeCl_3/C$, $SnCl_4/C$, $TaCl_5/C$, $SbCl_3/C$, $AlCl_3/C$, and $AlF_3/C$. The support for the metal halides listed can also be alumina or fluorinated alumina. All of the listed catalysts may be partially or totally fluorinated by anhydrous HF.

Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

Preferably the reactor is constructed from materials that are resistant to the corrosive effects of the HF and catalyst, such as Hastelloy-C, Inconel, Monel, Incolloy. Such vapor phase fluorination reactors are well known in the art.

HCC-240fa, HF, and oxygen are simultaneously fed to a vaporizer and then into the vapor phase reactor. Optionally oxygen co-feed can be introduced to the feed stream after the vaporizer but before the reactor. The reaction temperature is from about 150° to 450° C. and the reaction pressure is at from about 0 to 125 psig. The mole ratio of HF to HCC-240fa is greater than or equal to 3:1; preferably between 3:1 and 20:1, more preferably between 4:1 and 12:1, and most preferably between 5:1 and 10:1. The mole ratio of oxygen to HCC-240fa is less than or equal to 0.1:1, preferably between 0.07:1 and 0.005:1, and more preferably between 0.01:1 and 0.05:1.

The preferred catalyst in the reactor is fluorinated chrome oxide. The reactor effluent consisting of partially fluorinated intermediates and by-products, overfluorinated by-products, HF, 1233zd(E+Z), and HCl, exits the reactor and becomes available for product, HCFO-1233zd(E), recovery and recycle of intermediates and unreacted reactants by means known in the art.

After deactivation of the catalyst in the reactor it can be regenerated in-situ by heating to from 300° to 400° C. and passing an oxidizing agent such as $O_2$ or $Cl_2$ over it for a prescribed period of time.

EXAMPLE 1

This example illustrates the continuous vapor phase fluorination reaction of 1,1,1,3,3-pentachloropropane with hydrogen fluoride to form 1-chloro-3,3,3-trifluoropropene and hydrogen chloride in the presence of oxygen co-feed. The fluorination catalyst for the experiment was fluorinated $Cr_2O_3$.

HCC-240fa+3HF→1233zd+4HCl

A continuous vapor phase fluorination reaction system consisting of air, $N_2$, HF, and organic feed systems, feed vaporizer, superheater, two-inch inner diameter monel reactor, acid scrubber, drier, and product collection system was used. The reactor was loaded with 2135 grams of fluorinated $Cr_2O_3$ catalyst which equates to about 1.44 liters of catalyst (the total height of the catalyst bed was about 28 inches). A multipoint thermocouple was installed in the middle of the reactor. The reactor was then heated to a reaction temperature of about 275° C. with a nitrogen gas ($N_2$) purge going over the catalyst after the reactor had been installed in a constant temperature sand bath. The reactor was maintained at about 2 psig of pressure.

HF feed was introduced to the reactor (via the vaporizer and superheater) as a co-feed with the $N_2$ for 15 minutes when the $N_2$ flow was stopped. The HF flow rate was adjusted to 1.0 lb/hr and then 1, 1,1,3,3-pentachloropropane (HCC-240fa) feed was started to the reactor (via the vaporizer and superheater) at 1.5 lb/hr.

Next, the air co-feed was introduced (air flow was added before the vaporizer) at the rate of 179.4 $cm^3$/min resulting in the $O_2$ to HCC-240fa ration of 0.032:1. The feed rate of HCC-240fa was kept steady at about 1.5 lb/hr and HF feed was kept steady at 1.0 lb/hr for about a 7.2 to 1 mole ratio of HF to 240fa. Once the reaction started the catalyst bed temperature was adjusted to from about 328° to 332° C. The complete conversion of HCC-240fa was observed throughout this example.

During this example, it was noted that the internal catalyst bed temperature was higher than that of external reactor heater (sand bath) due to the exothermic character of HCC-240fa fluorination reaction. Also, since excess catalyst was used, a temperature gradient was observed throughout the catalyst bed. Initially, at the reaction start up, the highest temperature (hot-spot) was observed at the inlet of the reactor. The hot-spot position slowly moved through the catalyst bed as the continuous reaction progressed indicating at least a partial deactivation of the catalyst at the inlet of the reactor.

After the reaction hot-spot moved to the middle of the reactor (total length of catalyst bed was about 28 inches) two points (11 and 14 inches from the reactor inlet) inside catalyst bed were selected to monitor the rate of catalyst deactivation. As shown in FIG. 1, the temperatures at these two positions inside the catalyst bed were monitored for over 20 hours. It was calculated that the temperature at 11 inches was decreasing linearly at the rate of 0.04978° C./hr and the temperature at 14 inches was decreasing linearly at the rate of 0.05053° C./hr.

EXAMPLE 2

This example is a comparative example intended to illustrate the effect of oxygen co-feed on the chromium oxide catalyst stability during the continuous vapor phase fluorination reaction of 1,1,1,3,3-pentachloropropane with hydrogen fluoride to produce 1-chloro-3,3,3-trifluoropropene and hydrogen chloride.

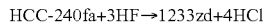

For this example the same reaction system and reaction conditions were used as in the Example 1 with the exception that at the completion of the experiment for Example 1, the air co-feed was stopped.

Figure 2:
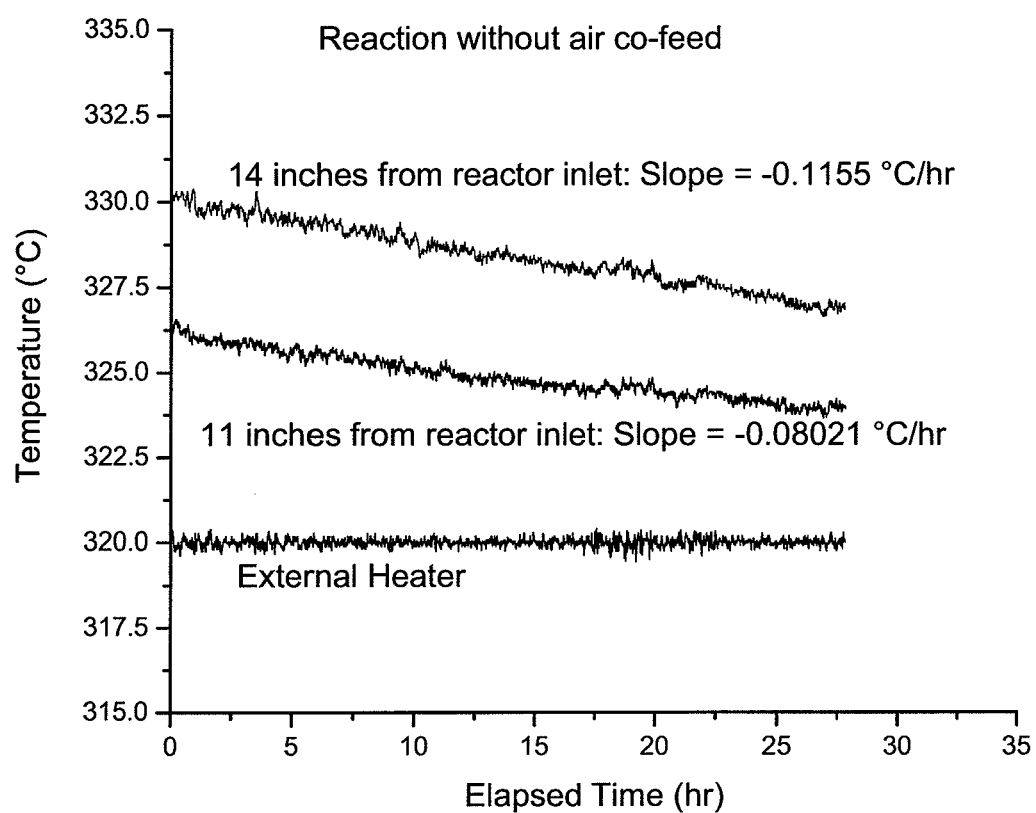
FIG. 2 illustrates the temperature profiles in the reactor without the air co-feed as measured at 11 and 14 inches from the inlet, compared to the temperature of the external sand bath heater over time.

After the air co-feed was stopped the temperature of the external heater was adjusted to bring the catalyst bed temperature, 14 inches from the reactor inlet, to about 330° C. Then, as in Example 1, and as shown in FIG. 2, the catalyst bed temperatures at positions 11 and 14 inches from the reactor inlet were monitored for over 20 hours. It was calculated that the temperature at 11 inches was decreasing linearly at the rate of 0.08021° C./hr and the temperature at 14 inches was decreasing linearly at the rate of 0.11550° C./hr.

Comparing FIG. 1 to FIG. 2, it is clear that the temperature measured at 11 and 14 inches inside catalyst bed in the absence of air co-feed decreased 1.6 and 2.3 times faster, respectively, than in the presence of air-co-feed. This indicates that the co-feed of oxygen together with HCC-240fa and HF to the fluorination reactor, even at a ratio of $O_2$ to HCC-240fa as low as 0.032 to 1 significantly decreased the rate of chromium oxide catalyst deactivation, by a factor of at least two fold (2×).

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A method of extending the lifetime of a catalyst used in the vapor phase catalytic fluorination reaction of the raw materials 1,1,1,3,3-pentachloro-propane (HCC-240fa) and hydrogen fluoride (HF) to produce 1-chloro-3,3,3-trifluoropropene, comprising the step of introducing an oxygen co-feed into the fluorination reaction, thereby extending the catalyst life during the fluorination reaction.

2. The method of claim 1, wherein the catalyst life is extended by at least two-fold.

3. The method of claim 1, wherein the oxygen is introduced together with the feeds of the raw materials 1,1,1,3,3-pentachloropropane and hydrogen fluoride.

4. The method of claim 1, wherein the oxygen is introduced after the raw materials 1,1,1,3,3-pentachloropropane and hydrogen fluoride have been vaporized.

5. The method of claim 1, wherein the oxygen is introduced before the raw materials 1,1,1,3,3-pentachloropropane and hydrogen fluoride have been vaporized.

6. The method of claim 1, wherein the source of oxygen is selected from the group consisting of oxygen gas, dry air, and oxygen gas diluted with an inert gas.

7. The method of claim 1, wherein the molar ratio of oxygen to 1,1,1,3,3-pentachloropropane is between 0.005 to 1 and 0.1 to 1.

8. The method of claim 1, wherein the molar ratio of oxygen to 1,1,1,3,3-pentachloropropane is between 0.01 to 1 and 0.07 to 1.

9. The method of claim 1, wherein the molar ratio of oxygen to 1,1,1,3,3-pentachloropropane is between 0.02 to 1 and 0.05 to 1.

10. The method of claim 1, wherein the catalyst is selected from the group consisting of chromium, aluminum, cobalt, manganese, nickel and iron oxides, hydroxides, halides, oxyhalides, inorganic salts thereof and their mixtures.

11. The method of claim 1, wherein the catalyst is selected from the group consisting of $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof.

12. The method of claim 1, wherein the catalyst comprises one or more chromium (III) oxides.

13. The method of claim 12, wherein the catalyst comprises crystalline chromium oxide.

14. The method of claim 12, wherein the catalyst comprises amorphous chromium oxide.

15. The method of claim 14, wherein the catalyst is at least partially fluorinated.

16. The method of claim 1, wherein the catalyst is selected from the group consisting of $FeCl_3$, $SnCl_4$, $TaCl_5$, $SbCl_3$, $AlCl_3$, and $AlF_3$, supported on carbon.

17. The method of claim 1, wherein the catalyst is selected from the group consisting of $FeCl_3$, $SnCl_4$, $TaCl_5$, $SbCl_3$, $AlCl_3$, and $AlF_3$, supported on alumina.

18. The method of claim 1, wherein the catalyst is selected from the group consisting of $FeCl_3$, $SnCl_4$, $TaCl_5$, $SbCl_3$, $AlCl_3$, and $AlF_3$, supported on fluorinated alumina.

19. A method of extending the lifetime of a catalyst used in the vapor phase catalytic fluorination reaction of the raw materials 1,1,1,3,3-pentachloro-propane and hydrogen fluoride to produce 1-chloro-3,3,3-trifluoropropene, comprising the steps of:
(a) monitoring the exotherm of the active catalyst relative to the external reactor heater, and
(b) adding an oxygen co-feed into the fluorination reaction to retard the deactivation of the catalyst during the fluorination reaction.

20. The method of claim 19, wherein the oxygen co-feed retards the deactivation of the catalyst compared to when no oxygen co-feed is employed.

* * * * *